(12) United States Patent
McShane et al.

(10) Patent No.: US 7,989,432 B2
(45) Date of Patent: *Aug. 2, 2011

(54) MICELLES

(75) Inventors: James McShane, Wake Forest, NC (US); Tori Arens, Raleigh, NC (US); Kazuhiro Kaneko, Ibaraki (JP); Tomohiro Watanabe, Ibaraki (JP); Kazuhide Ashizawa, Ibaraki (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/142,608

(22) Filed: Jun. 19, 2008

(65) Prior Publication Data

US 2009/0136564 A1    May 28, 2009

Related U.S. Application Data

(63) Continuation of application No. 11/106,654, filed on Apr. 15, 2005, now Pat. No. 7,390,793, which is a continuation of application No. 10/204,227, filed as application No. PCT/US01/05297 on Feb. 20, 2001, now Pat. No. 6,906,042.

(60) Provisional application No. 60/183,768, filed on Feb. 18, 2000.

(51) Int. Cl.
*A61K 31/70* (2006.01)

(52) U.S. Cl. ......................................... 514/53; 424/400

(58) Field of Classification Search ........................ None
See application file for complete search history.

(56) References Cited

U.S. PATENT DOCUMENTS

| | | | | |
|---|---|---|---|---|
| 5,681,824 A | * | 10/1997 | Christ et al. ........... | 514/53 |
| 5,750,664 A | * | 5/1998 | Christ et al. ........... | 536/17.2 |
| 5,935,938 A | | 8/1999 | Christ et al. | |
| 5,952,309 A | | 9/1999 | Rossignol et al. | |
| 6,184,366 B1 | | 2/2001 | Christ et al. | |
| 6,235,724 B1 | | 5/2001 | Asai et al. | |
| 6,417,172 B1 | | 7/2002 | Rossignol et al. | |
| 6,643,950 B2 | | 11/2003 | Lambert et al. | |
| 6,683,063 B2 | | 1/2004 | Rossignol et al. | |
| 6,861,512 B2 | | 3/2005 | Lu et al. | |
| 6,906,042 B2 | * | 6/2005 | McShane et al. ........ | 514/53 |
| 7,348,316 B2 | | 3/2008 | Rossignol et al. | |
| 7,390,793 B2 | * | 6/2008 | McShane et al. ........ | 514/53 |
| 7,727,974 B2 | | 6/2010 | Kawano et al. | |
| 7,737,129 B2 | | 6/2010 | Christ et al. | |

FOREIGN PATENT DOCUMENTS

WO        WO 98/55106        12/1998

OTHER PUBLICATIONS

U.S. Appl. No. 09/774,541, filed Jan. 30, 2001, Abandoned.
U.S. Appl. No. 10/144,670, filed May 13, 2002, Abandoned.
U.S. Appl. No. 12/781,166, filed May 17, 2010, Pending.
U.S. Appl. No. 12/142,608, filed Jun. 19, 2008, Pending.
U.S. Appl. No. 09/889,274, filed Jul. 12, 2001, Abandoned.
U.S. Appl. No. 11/010,550, filed Dec. 13, 2004, Pending.
U.S. Appl. No. 09/879,718, filed Jun. 11, 2001, Abandoned.
U.S. Appl. No. 10/171,478, filed Jun. 13, 2002, Abandoned.
U.S. Appl. No. 10/486,455, filed Jul. 26, 2004, Abandoned.
U.S. Appl. No. 11/958,243, filed Dec. 17, 2007, Pending.
U.S. Appl. No. 10/478,459, filed Jun. 1, 2004, Pending.
U.S. Appl. No. 12/816,913, filed Jun. 16, 2010, Pending.
U.S. Appl. No. 12/775,574, filed May 7, 2010, Pending.
U.S. Appl. No. 10/546,132, filed Dec. 12, 2005, Pending.
U.S. Appl. No. 10/344,183, filed Jun. 5, 2003, Pending.
U.S. Appl. No. 12/516,082, filed Dec. 10, 2009, Pending.
U.S. Appl. No. 12/064,450, filed Feb. 21, 2008, Pending.
Asai et al., J. Pharm. Pharmacol. 51: 577-84, 1999.
Asai et al., Drug Dev. Ind. Pharm. 25 (9): 975-82, 1999.
Asai et al., Drug Dev. Ind. Pharm. 25 (10): 1107-13, 1999.
Asai et al., Drug Dev. Ind. Pharm. 26 (4): 383-90, 2000.
Asai et al., Int'l J. Pharm. 170: 73-84, 1999.
Asai et al., Chemistry and Physics of Lipids, 97: 93-104, 1999.

* cited by examiner

*Primary Examiner* — Elli Peselev
(74) *Attorney, Agent, or Firm* — McCarter & English, LLP (57) ABSTRACT

The present invention provides micelles, solutions comprising micelles, methods for preparing micelles, and methods for delivering micelles to patients. The micelles have fixed, preselected hydrodynamic diameters and are formed from basic or acidic amphiphilic compounds.

37 Claims, 3 Drawing Sheets

MICELLES

RELATED APPLICATIONS

This application is a continuation of U.S. application Ser. No. 11/106,654 filed Apr. 15, 2005, now U.S. Pat. No. 7,390,793, which is a continuation of U.S. application Ser. No. 10/204,227 now U.S. Pat. No. 6,906,042, filed Oct. 3, 2002, which claims priority under §371 to PCT/US01/05297 filed Feb. 20, 2001, which claims priority to U.S. Provisional Application No. 60/183,768 filed Feb. 18, 2000. The contents of each of these applications are expressly incorporated herein by this reference.

FIELD OF THE INVENTION

The present invention provides micelles, solutions comprising micelles, methods for preparing micelles, and methods for delivering micelles to patients. The micelles have fixed, preselected hydrodynamic diameters and are formed from basic or acidic amphiphilic compounds.

BACKGROUND OF THE INVENTION

Amphiphilic compounds are compounds with hydrophilic (water-loving) and hydrophobic (water-fearing) regions. When dispersed in water at a concentration above their critical micelle concentration or "CMC," amphiphilic compounds spontaneously self-associate into micelles. Micelles have a size which depends on properties of the solvent in which they are dispersed. The size of micelles can vary from approximately two to several hundreds of nanometers in equivalent spherical diameter.

When a drug is an amphiphilic compound which forms micelles when formulated for intravenous administration, the pharmacokinetics of the drug can depend upon the size of the micelle formed. Pharmacokinetics describes the time course of the distribution of a drug within the body after administration. The pharmacokinetics of a drug can affect its efficacy, metabolism, distribution, and/or toxicity in the body, either positively or negatively. For other routes of administration, micelle size can also influence pharmacokinetics. When the drug is in the form of a micelle, the effectiveness of delivery of the drug to the site of action depends upon the size of the aggregate, as the micelle size might affect diffusion, transport across cell membranes, and interactions with enzymes, transport proteins and lipids.

Prior to the work of the present inventors, the micelle size of amphiphilic drug compounds in water was known to be governed by the state of the solution, so once the formulation of the drug was chosen, a predetermined micelle size distribution was expected to result. The ability to control the micelle size of a drug delivered in a pharmaceutical formulation was severely limited, and control of the rate of delivery of drug to the site of action, therefore, was limited due to the inability to control the size of the micelle in solutions.

There is a need in the art to control or fix the size of micelles formed by amphiphilic drug compounds in aqueous solutions so that drug delivery rates and pharmacokinetics can be controlled. The present invention is directed to these, as well as other, important ends.

SUMMARY OF THE INVENTION

The present invention provides methods for preparing micelles comprising providing an amount of least one acidic amphiphilic compound, wherein the acidic amphiphilic compound comprises at least one ionizable group; adding the acidic amphiphilic compound to a first aqueous alkaline solution; wherein the first aqueous alkaline solution comprises at least one basic metal salt and at least one neutral metal salt; wherein the first aqueous alkaline solution has a predetermined metal ion concentration; wherein the concentration of acidic amphiphilic compound in the first aqueous solution is higher than the critical micelle concentration of the acidic amphiphilic compound; and wherein the pH and the metal ion concentration of the first aqueous alkaline solution are effective to form micelles with a preselected hydrodynamic diameter; thereby forming a second aqueous solution comprising micelles of the acidic amphiphilic compound with a preselected hydrodynamic diameter. The methods may further comprise adding the second aqueous alkaline solution to a third aqueous solution, wherein the third aqueous solution comprises a buffer system or at least one strong acid; thereby forming a fourth aqueous solution having a neutral pH relative to the pH of the second aqueous alkaline solution, wherein the micelles in the fourth aqueous solution have a fixed, preselected hydrodynamic diameter that is substantially the same as the fixed, preselected hydrodynamic diameter of the micelles in the second aqueous alkaline solution.

The present invention also provides methods for preparing micelles comprising providing an amount of at least one basic amphiphilic compound that comprises at least one ionizable group; adding the basic amphiphilic compound to a first aqueous acidic solution; wherein the first aqueous solution comprises at least one protic acidic and at least one neutral metal salt; wherein the first aqueous solution has a predetermined metal ion concentration; wherein the concentration of basic amphiphilic compound in the first aqueous solution is higher than the critical micelle concentration of the basic amphiphilic compound; wherein the acidic pH and the metal ion concentration of the first aqueous solution are effective to form micelles with a preselected hydrodynamic diameter; thereby forming a second aqueous solution comprising micelles of the acidic amphiphilic compound with a preselected hydrodynamic diameter. The methods may further comprise adding the second aqueous solution to a third aqueous solution, wherein the third aqueous solution comprises a buffer system or at least one strong base; thereby forming a fourth aqueous solution having a neutral pH relative to the pH of the second aqueous acidic solution, wherein the micelles in the fourth aqueous solution have a fixed, preselected hydrodynamic diameter that is substantially the same as the fixed, preselected hydrodynamic diameter of the micelles in the second aqueous acidic solution.

The present invention also provides novel micelles, novel aqueous solutions comprising micelles, and novel methods of delivering micelles and/or aqueous solutions comprising micelles to patients.

These and other aspects of the present invention are described in detail below.

DETAILED DESCRIPTION OF THE INVENTION

Amphiphilic compounds, as used herein, refer to compounds with hydrophilic and hydrophobic moieties, which form micelles when dispersed in aqueous solutions. The amphiphilic compounds of the invention preferably comprise at least one ionizable group.

Critical micelle concentration ("CMC"), as used herein, is the concentration of amphiphilic compound at which micelles begin to spontaneously form in an aqueous solution. A "low" critical micelle concentration is preferably less than $10^{-6}$ g/ml.

Micelle, as used herein, refers to any water soluble aggregate which is spontaneously and reversibly formed from amphiphilic compounds or ions.

Hydrodynamic diameter of a micelle indicates that the micelle has the same hydrodynamic properties (e.g., diffusion coefficient) as a sphere of the same diameter. For example, a micelle having a width of 5 nm and a length of 9 nm might have a hydrodynamic diameter of 7 nm.

The present inventors have discovered a method for preparing micelles with fixed (i.e., stable), preseselected hydrodynamic diameters where the hydrodynamic diameter of micelles formed at an acidic or basic pH remains substantially the same at the acidic or basic pH; and the hydrodynamic diameter of the micelles remains substantially the same after adjustment of the acidic or basic pH to a second more neutral pH value (i.e., a neutral relative to the acidic or basic pH), where it would normally be expected that the hydrodynamic diameter of the micelles would increase. This discovery provides methods to produce pharmaceutical formulations of micelles with fixed, preselected hydrodynamic diameters. Using the methods of the invention, micelles having optimal hydrodynamic diameters can be used to design drug formulations that yield optimally desired pharmacokinetic and drug delivery properties.

The methods described herein are applicable to all acidic or basic amphiphilic compounds for which the critical micelle concentration is low. Preferably the acidic or basic amphiphilic compounds comprise at least one ionizable group. For formulations where the critical concentration is low, the salt concentration of the drug formulation must be kept sufficiently low to provide the required stability of the hydrodynamic diameter of the micelles. Thus, the stability of the hydrodynamic diameter of the micelles formed from such a process is governed by the critical micelle concentration and the pair inter-particle potential energy.

The micelles can grow in hydrodynamic diameter via a monomer mediated process similar to crystal ripening. The rate of hydrodynamic diameter increase is proportional to the monomer concentration (i.e., critical micelle concentration). For systems with a low critical micelle concentration, the rate of micelle hydrodynamic diameter increase via this mechanism can be sufficiently slow to allow the micelles to be stable for the amount of time required to be useful as pharmaceutical products.

Figure 1:
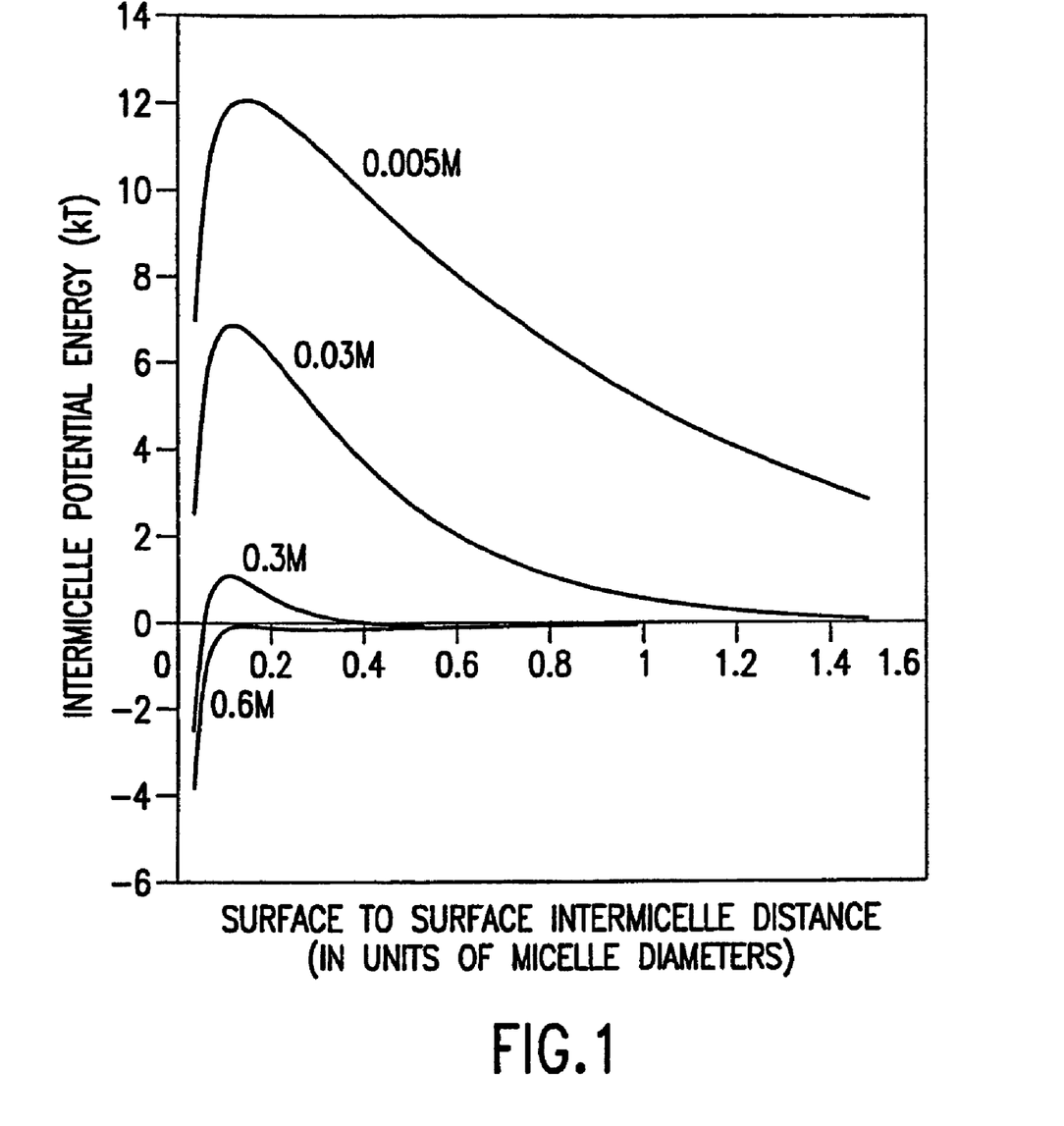
FIG. 1 is a graph showing the relationship between $V_{max}/kT$ and salt concentration.

Micelles can also grow in hydrodynamic diameter via an aggregation and fusion mechanism which is governed by particle interaction potential energy. The tendency for aggregation can be expressed as a stability ratio W. The stability of the micelles increases with W. W is inversely related to the salt concentration of the solution and directly related to the electrostatic charge of the micelle. Therefore, as the salt concentration in solution is lowered and/or the electrostatic charge of the micelle is increased, the stability of the micelles is increased relative to growth from an aggregation-fusion mechanism. FIG. 1 shows how, at salt concentrations greater than 0.6 M, the maximum interaction potential energy ($V_{max}$) between micelles is zero and the aggregation rate is only diffusion limited. As the salt concentration is decreased, however, $V_{max}/kT$ increases and the aggregation rate decreases accordingly. Therefore, salt concentration can be adjusted to impart the necessary stability to the system.

To attain the desired micelle hydrodynamic diameter using an acidic amphiphilic compound, the acidic amphiphilic compound is dissolved in an aqueous alkaline solution at a predetermined pH value and a constant metal ion concentration. The pH must be higher than the pKa of the at least one ionizable group of the acidic amphiphilic compound. The aqueous alkaline solution is prepared by adding at least one basic metal salt, at least one neutral metal salt, and a predetermined metal ion concentration to an aqueous solution. Preferably the basic metal salt and the neutral metal salt have the same metal ion. Typical metal ions include, without limitation, $Ca^{2+}$, $Mg^{2+}$, $Ba^+$, $Fe^{3+}$, $Fe^{3+}$, $Al^{3+}$, $Mn^{2+}$, $Mn^{2+}$, $Zn^{2+}$, $Cu^{3+}$, $Cu^+$, $Ni^{2+}$, $Sn^{2+}$, $Na^+$, $Li^+$, $K^+$ and the like. Preferred metal ions include $Na^+$, $K^+$, $Li^+$, $Ca^{2+}$, $Ba^+$, $Mg^{2+}$, and $Al^{3+}$. Typical basic metal salts useful in the present invention are, for example, the oxide and hydroxide salts of the aforementioned metal ions. Typical neutral metal salts useful in the present invention include, for example, halide salts (e.g., chloride, fluoride, bromide, iodide) of the aforementioned metal ions. Adding the acidic amphiphilic compound to the aqueous alkaline solution results in micelles with a fixed, preselected hydrodynamic diameter. "Fixed" means that the hydrodynamic diameter is stable (i.e., does not substantially change), and "preselected" means that hydrodynamic diameter was chosen for its optimal or desired pharmacokinetic and/or other properties.

To attain the desired micelle hydrodynamic diameter using a basic amphiphilic compound, the basic amphiphilic compound is dissolved in an aqueous acid solution at a predetermined pH value and a constant metal ion concentration. The pH value must be lower than the pKa of the at least one ionizable group of the basic amphiphilic compound. The aqueous acidic solution is prepared by adding at least one protic acid, at least one neutral metal salt, and a predetermined metal ion concentration to an aqueous solution. Preferably the protic acid and the neutral metal salt have the same metal ion. Typical metal ions include, without limitation, $Ca^{2+}$, $Mg^{2+}$, $Ba^{2+}$, $Fe^{2+}$, $Fe^{3+}$, $Al^{3+}$, $Mn^{3+}$, $Mn^{2+}$, $Zn^{2+}$, $Cu^{2+}$, $Cu^+$, $Ni^{2+}$, $Sn^{2+}$, $Na^+$, $Li^+$, $K^+$ and the like. Preferred metal ions include $Na^+$, $K^+$, $Li^+$, $Ca^{2+}$, $Ba^+$, $Mg^{2+}$, and $Al^{3+}$. Typical protic acid useful in the present invention are, for example, hydrochloric acids, phosphoric acids, sulfuric acids, acetic acids, citric acids, carbonic acids and the like. Typical neutral metal salts useful in the present invention include, for example, halide salts (e.g., chloride, fluoride, bromide, iodide) of the aforementioned metal ions. Adding the basic amphiphilic compound to the aqueous acid solution results in micelles with a fixed, preselected hydrodynamic diameter.

The concentration of the amphiphilic compound in the aqueous alkaline or acidic solution will be higher than the critical micelle concentration of the amphiphilic compound. The conditions which yield micelles of a preselected hydrodynamic diameter can be determined by preparing micelles in a matrix of pH values and salt concentrations. Different micelle hydrodynamic diameters result from the preparation of micelles in solutions with different pH values and salt concentrations. Thereafter, a solution comprising micelles with a fixed, preselected hydrodynamic diameter can be prepared based on the selected concentration of the acidic or basic amphiphilic compound, the pH, and the concentration of metal ions.

In addition to the above, the inventors have unexpectedly discovered that the hydrodynamic diameter of the micelles in the aqueous acidic or alkaline solution will remain substantially the same when the pH of the aqueous acidic or alkaline solution is neutralized (i.e., wherein ionizable groups in the amphiphilic compound are neutralized relative to the charged ionizable groups in the amphiphilic compound).

In particular, an aqueous solution comprising a buffer system and/or at least one strong acid is added to the aqueous alkaline solution comprising the micelles of the acidic amphiphilic compound in an amount sufficient to produce an aqueous solution having a neutral pH relative to the pH of the aqueous alkaline solution. The hydrodynamic diameter of the micelles in the aqueous solution having the relatively neutral pH will remain substantially the same as the hydrodynamic diameter of the micelles in the aqueous alkaline solution.

In another embodiment, an aqueous solution comprising a buffer system and/or at least one strong base is added to the aqueous acid solution comprising the micelles of the basic amphiphilic compound in an amount sufficient to produce an aqueous solution having a neutral pH relative to the pH of the aqueous acidic solution. The hydrodynamic diameter of the micelles in the aqueous solution having the relatively neutral pH will remain substantially the same as the hydrodynamic diameter of the micelles in the aqueous acid solution.

In the present invention, the terms "basic" or "alkaline" pH and "neutral" pH are relative terms. For example, when the first aqueous solution has a basic or alkaline pH, and the final aqueous solution has a neutral pH, the neutral pH is neutral relative to the pH of the basic or alkaline solution. In other words, the pH of the neutral solution is lower than the pH of the alkaline solution. More preferably, when the first aqueous solution has a basic or alkaline pH, the pH is from about 9 to about 13, more preferably from about 10 to about 12. Relative to the first alkaline solution, the neutral pH is preferably from about 4 to less than 9, more preferably from about 6 to less than 9, even more preferably from about 7 to less than 9, still more preferably from about 7 to about 8, most preferably about 7.4 to about 7.6.

Similarly, the terms "acidic" pH and "neutral" pH are relative terms. For example, when the first aqueous solution has an acidic pH, and the final aqueous solution has a neutral pH, the neutral pH is neutral relative to the pH of the acidic solution. In other words, the pH of the neutral solution is higher than the pH of the acidic solution. More preferably, when the first aqueous solution has an acidic pH, the pH is from about 1 to about 6, more preferably from about 3 to about 5. Relative to the first acidic solution, the neutral pH is preferably more than 6 to about 13, more preferably from about 7 to about 9, still more preferably from about 7 to about 8, most preferably about 7.4 to about 7.6.

When the hydrodynamic diameter of the micelles in the aqueous solution having the relatively neutral pH remains "substantially the same" as the hydrodynamic diameter of the micelles in the aqueous alkaline or acidic solution, "substantially the same" means that the hydrodynamic diameter of the micelles in the relatively neutral solution does not change by more than 4 nm, more preferably does not change by more than 2 nm, still more preferably does not change by more than 1 nm, even more preferably does not change by more than 0.5 nm, and most preferably does not change at all from the hydrodynamic diameter of the micelles in the alkaline or acidic solution.

The buffer system may be any known in the art including, for example, phosphate buffers, acetate buffers, citrate buffers, maleate buffers, carbonate buffers, bicarbonate buffers, tartrate buffers, tromethamine buffers, triethanolamine buffers, meglumine buffers and the like. The strong acid can by any known in the art including, for example, hydrochloric acid, sulfuric acid, phosphoric acid and the like. The strong base can be any known in the art including, for example, sodium hydroxide, potassium hydroxide and the like.

The hydrodynamic diameter of the micelles of the present invention can be from about 1 nm to about 100 nm, preferably from about 5 nm to about 50 nm, more preferably from about 6 nm to about 20 nm, even more preferably from about 7 nm to about 15 nm, and most preferably from about 7 nm to about 9 nm.

The hydrodynamic diameter of micelles of the present invention preferably refers to a range of hydrodynamic diameters of about 5 nm, preferably about 4 nm, more preferably about 3 nm, most preferably about 2 nm or about 1 nm. For example, with respect to a hydrodynamic diameter range of about 2 nm, the hydrodynamic diameter can be from about 7 nm to about 9 nm. Alternatively, the hydrodynamic diameter can be from about 2 nm to about 4 nm; or from about 3 nm to about 5 nm; or from about 4 nm to about 6 nm; or from about 5 nm to about 7 nm; or from about 6 nm to about 8 nm; or from about 8 nm to about 10 nm; or from about 9 nm to about 11 nm; or from about 10 nm to about 12 nm; or from about 11 nm to about 13 nm; or from about 12 nm to about 14 nm; or from about 13 nm to about 15 nm; or from about 14 nm to about 16 nm; or from about 15 nm to about 17 nm; or from about 16 nm to about 18 nm; or from about 17 nm to about 19 nm; or from about 18 nm to about 20 nm; or from about 19 nm to about 21 nm; or from about 20 nm to about 22 nm; or from about 21 nm to about 23 nm; or from about 22 nm to about 24 nm; or from about 23 nm to about 25 nm; or from about 24 nm to about 26 nm. In other words, the 2 nm range (or the 5 nm range or the 4 nm range or the 3 nm range or the 1 nm range) can be anywhere in the range of from about 1 nm to about 100 nm; preferably from about 5 nm to about 50 nm, more preferably from about 6 nm to about 20 nm, even more preferably from about 7 nm to about 15 nm, and most preferably from about 7 nm to about 9 nm.

The hydrodynamic diameter of micelles also means that substantially all the micelles have about the same hydrodynamic diameter (i.e., or range of hydrodynamic diameters as described above). "Substantially all the micelles have about the same hydrodynamic diameter" generally means that more than 50% of the micelles have a hydrodynamic diameter that falls within the range as described above; preferably more than 60%, 70% or 80% of the micelles have a hydrodynamic diameter that falls within the range as described above; even more preferably about 90%, about 95%, or about 99% of the micelles have a hydrodynamic diameter that falls within the range as described above; most preferably 100% of the micelles have a hydrodynamic diameter that falls within the range as described above.

Acidic or basic amphiphilic compounds for use in the present invention include any acidic or basic amphiphilic compound known in the art. Preferably the acidic or basic amphiphilic compound comprises at least one ionizable group. The at least one ionizable group of the acidic amphiphilic compound can be, for example, phosphoric acids, carboxylic acids, sulfuric acids, sulfonic acids, sulfinic acids, thiols, alcohols, enols and the like. The at least one ionizable group of the basic amphiphilic compound can be, for example, amines, phosphines, and the like.

Exemplary acidic or basic amphiphilic compounds comprising at least one ionizable group include the compounds described in WO 96/39411 and U.S. Pat. Nos. 5,530,113, 5,681,824, 5,750,664, 5,935,938, and 6,184,366, the disclosures of which are incorporated by reference herein in their entirety. These compounds are generally represented by Formula (A), pharmaceutically acceptable salts thereof, and/or stereoisomers (including enantiomers and/or diastereomers) thereof:

(A)

wherein $R^1$ is selected from the group consisting of:

J, K and Q are each independently a straight or branched $C_{1-5}$ alkyl;
L is O, N or C;
M is O or N;
G is N, O, S, SO or $SO_2$;
$R^2$ is a straight or branched $C_{5-15}$ alkyl;
$R^3$ is selected from the group consisting of:

E is N, O, S, SO or $SO_2$;
A, B and D are each independently a straight or branched $C_{1-15}$ alkyl group;
$R^4$ is a straight or branched $C_{4-20}$ alkyl group or

U and V are each independently a straight or branched $C_{2-15}$ alkyl group;
W is a hydrogen or a straight or branched $C_{1-5}$ alkyl group;
$R^5$ is hydrogen, -J', -J'-OH, -J'-O—K', -J'-O—K'—OH or J'-O—PO(OH)$_2$;
J' and K' are each independently a straight or branched $C_{1-5}$ alkyl group;
$R^6$ is hydroxy, halogen, a $C_{1-5}$ alkoxy group or a $C_{1-5}$ acyloxy group;
$A^1$ and $A^2$ are each independently selected from the group consisting of:

Z is a straight or branched $C_{1-10}$ alkyl group.

The term "alkyl" refers to aliphatic organic groups which may be branched or straight and which may optionally be substituted with one or more halogen atoms at any position along the alkyl chain. The term "pharmaceutically acceptable salt" includes salts of compounds derived from the combination of the compound and an organic or inorganic acid or base.

A preferred compound of Formula (A) is Compound (I), pharmaceutically acceptable salts thereof, and/or stereoisomers (including enantiomers and/or diastereomers) thereof:

(1)

In a preferred embodiment, Compound (1) is Compound (1A) or a pharmaceutically acceptable salt thereof, which is represented by the following formula:

(1A)

When Compound 1A is a sodium salt (i.e., both hydrogen atoms in both —OPO(OH)$_2$ groups are replaced with sodium), then the compound is E5564.

Other preferred compounds described in WO 96/39411 and U.S. Pat. Nos. 5,530,113, 5,681,824, 5,750,664, 5,935,938, and 6,184,366 for use in the present invention include those of Formula (B), pharmaceutically acceptable salts thereof, and/or stereoisomers (including enantiomers and/or diastereomers) thereof:

(B)

wherein R$^1$, R$^3$ and R$^4$ are as defined below:

| # | R$^1$ | R$^3$ | R$^4$ |
|---|---|---|---|
| 1 | COCH$_2$CO(CH$_2$)$_{10}$CH$_3$ | CO(CH$_2$)$_9$CH=CH(CH$_2$)$_5$CH$_3$ | (CH$_2$)$_2$CH(OCH$_3$)(CH$_2$)$_6$CH$_3$ |
| 2 | COCH$_2$CO(CH$_2$)$_{10}$CH$_3$ | CO(CH$_2$)$_9$CH=CH(CH$_2$)$_5$CH$_3$ | (CH$_2$)$_2$CH(OH)(CH$_2$)$_6$CH$_3$ |
| 3 | COCH$_2$CO(CH$_2$)$_{10}$CH$_3$ | CO(CH$_2$)$_{16}$CH$_3$ | (CH$_2$)$_2$CH(OH)(CH$_2$)$_6$CH$_3$ |
| 4 | COCH$_2$CHOH(CH$_2$)$_{10}$CH$_3$ | CO(CH$_2$)$_9$CH=CH(CH$_2$)$_5$CH$_3$ | (CH$_2$)$_2$CH(OH)(CH$_2$)$_6$CH$_3$ |
| 5 | COCH$_2$CO(CH$_2$)$_{10}$CH$_3$ | CO(CH$_2$)$_9$CH=CH(CH$_2$)$_5$CH$_3$ | (CH$_2$)$_9$CH$_3$ |
| 6 | CO(CH$_2$)$_9$CH=CH(CH$_2$)$_5$CH$_3$ | CO(CH$_2$)$_9$CH=CH(CH$_2$)$_5$CH$_3$ | (CH$_2$)$_2$CH(OH)(CH$_2$)$_6$CH$_3$ |
| 7 | CO(CH$_2$)$_{12}$CH$_3$ | CO(CH$_2$)$_9$CH=CH(CH$_2$)$_5$CH$_3$ | (CH$_2$)$_2$CH(OH)(CH$_2$)$_6$CH$_3$ |
| 8 | COCH$_2$CH(OCH$_3$)(CH$_2$)$_{10}$CH$_3$ | CO(CH$_2$)$_9$CH=CH(CH$_2$)$_5$CH$_3$ | (CH$_2$)$_2$CH(OCH$_3$)(CH$_2$)$_6$CH$_3$ |
| 9 | COCH$_2$CH(OCH$_3$)(CH$_2$)$_{10}$CH$_3$ | CO(CH$_2$)$_9$CH=CH(CH$_2$)$_5$CH$_3$ | (CH$_2$)$_2$CH(OH)(CH$_2$)$_6$CH$_3$ |
| 10 | COCH$_2$CH(OH)(CH$_2$)$_{10}$CH$_3$ | CO(CH$_2$)$_9$CH=CH(CH$_2$)$_5$CH$_3$ | (CH$_2$)$_2$CH(OCH$_3$)(CH$_2$)$_6$CH$_3$ |
| 11 | COCH$_2$CO(CH$_2$)$_{10}$CH$_3$ | CO(CH$_2$)$_9$CH=CH(CH$_2$)$_5$CH$_3$ | (CH$_2$)$_2$CH(OCH$_3$)(CH$_2$)$_6$CH$_3$ | wherein R$_A$ in Compounds (1)-(10) is CH$_2$OCH$_3$ and R$_A$ in Compound (II) is CH$_3$.

Methods for making Compounds (I) and (1A) and the compounds of Formulas (A) and (B) are described in WO 96/39411 and U.S. Pat. Nos. 5,530,113, 5,681,824, 5,750,664, 5,935,938, and 6,184,366, the disclosures of which are incorporated by reference herein in their entirety.

The lipopolysaccharides described in WO 96/39411 and U.S. Pat. Nos. 5,530,113, 5,681,824, 5,750,664, 5,935,938, and 6,184,366 are useful for treating and/or preventing any lipopolysaccharide-mediated disorder in a patient in need thereof including, for example, sepsis, septicemia (e.g., endotoxemia), endotoxemia associated with gram negative bacteria (with its accompanying symptoms of fever, generalized inflammation, disseminated intravascular coagulation, hypotension, renal dysfunction and acute renal failure, acute respiratory distress syndrome, adult respiratory distress syndrome, hepatocellular destruction and/or cardiac failure), and various forms of septic shock (e.g., endotoxic shock). The lipopolysaccharides described in these patents and publication are also useful for treating or preventing localized or systemic inflammatory response to infection by different types of organisms in a patient in need thereof, including gram negative bacteria, and in diseases related to translocation of gram negative bacteria or endotoxin from the gut. Together these disorders are termed systemic inflammatory response syndrome or SIRS. "Patient" includes animals, preferably mammals, more preferably humans.

The compounds described in WO 96/39411 and U.S. Pat. Nos. 5,530,113, 5,681,824, 5,750,664, 5,935,938, and 6,184,366 are administered in dosages which provide suitable inhibition of lipopolysaccharide activation of target cells; generally, these dosages are, preferably between 0.01-50 mg/patient, more preferably, between 0.05-25 mg/patient and most preferably, between 1-12 mg/patient. Most preferably the dosages are administered over three to six days as a continuous infusion or as an intermittent dosing to obtain desired plasma concentrations. It will be understood, however, that the specific dose level for any particular patient will depend on a variety of factors including the activity of the specific compound used; the age, weight, general health, and sex of the patient being treated; the time and route of administration; the rate of excretion; other drugs which have previously been administered; and the severity of the particular disease being treated.

The micelles of the present invention and the solutions comprising micelles can be used for treating or preventing any disease or disorder that the amphiphilic compounds are known to be useful for treating or preventing. As discussed above, for example, E5564 is known to be useful for treating sepsis. In the present invention, the micelles and solutions comprising micelles are preferably administered parenterally, although other forms of administration can be used (e.g., oral, topical, transdermal, ocular). The term parenteral as used herein includes subcutaneous, intravenous, intramuscular, and intraarterial injections with a variety of infusion techniques. Intraarterial and intravenous injection as used herein includes administration through catheters. Preferred for certain indications are methods of administration which allow rapid access to the tissue or organ being treated, such as intravenous injections for the treatment of endotoxemia when using E5564.

Pharmaceutical compositions containing the active ingredient may be in any form suitable for the intended method of administration. Aqueous solutions and/or suspensions of the invention contain the active materials in admixture with excipients suitable for the manufacture thereof. Such excipients include a suspending agent, such as sodium carboxymethylcellulose, methylcellulose, hydroxypropylmethyl cellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadeaethyleneoxycetanol), a condensation product of ethylene oxide with a partial ester derived from a fatty acid and a hexitol anhydride (e.g., polyoxyethylene sorbitan mono-oleate). The aqueous suspension may also contain one or more preservative such as ethyl of n-propyl p-hydroxybenzoate.

The pharmaceutical compositions of the invention are preferably in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Formulations suitable for parenteral administration include aqueous and non-aqueous isotonic sterile injection solutions which may contain anti-oxidants, buffers, bacteriostats and solutes which render the formation isotonic with the blood of the intended recipient; and aqueous and non-aqueous sterile suspensions which may include suspending agents and thickening agents. The formulations may be presented in unit-dose or multi-dose sealed containers, for example, ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders of the kind previously described.

When using a lyophilized drug product, clinicians typically reconstitute the freeze-dried preparation in physiologically acceptable solutions. It is desirable to be able to store the reconstituted solution either at room temperature or under refrigeration. Freeze-dried preparations of the micelles described herein are rehydratable with water or an aqueous dextrose solution suitable for intravenous administration, with the micelle hydrodynamic diameter distribution remaining unchanged. Such reconstituted micelle solutions can be stored at room temperature or refrigerated temperatures with no change in the micelle hydrodynamic diameter.

EXAMPLES

The following examples are for purposes of illustration only, and are not intended to limit the scope of the appended claims.

Example 1

E5564 is a lipopolysaccharide analog comprising two sugar moieties and four long chain fatty acid moieties and has a molecular weight of about 1,401. Methods for preparing E5564 are described in U.S. Pat. Nos. 5,530,113, 5,681,824, 5,750,664, 5,935,938, and 6,184,366, and WO 96/39411, the disclosures of which are incorporated by reference herein in their entirety. E5564 drug formulations with varying micelle hydrodynamic diameters, achieved by control of the pH and concentration of counter ions (e.g., sodium), were produced as follows.

E5564 was dissolved in an NaOH solution for 60 minutes. The pH of the NaOH solution can be varied from 9 to 13 by varying the NaOH and NaCl concentrations, such that the concentration of $Na^+$ in each solution was kept constant at 0.01 M. The concentration of $Na^+$ in the solution can be in the range from about 0 to 0.6 M, preferably from about 0.001 M to about 0.6 M. The E5564/NaOH solution was then combined with a phosphate buffer solution to yield a solution with a pH of 7.5.

Figure 3:
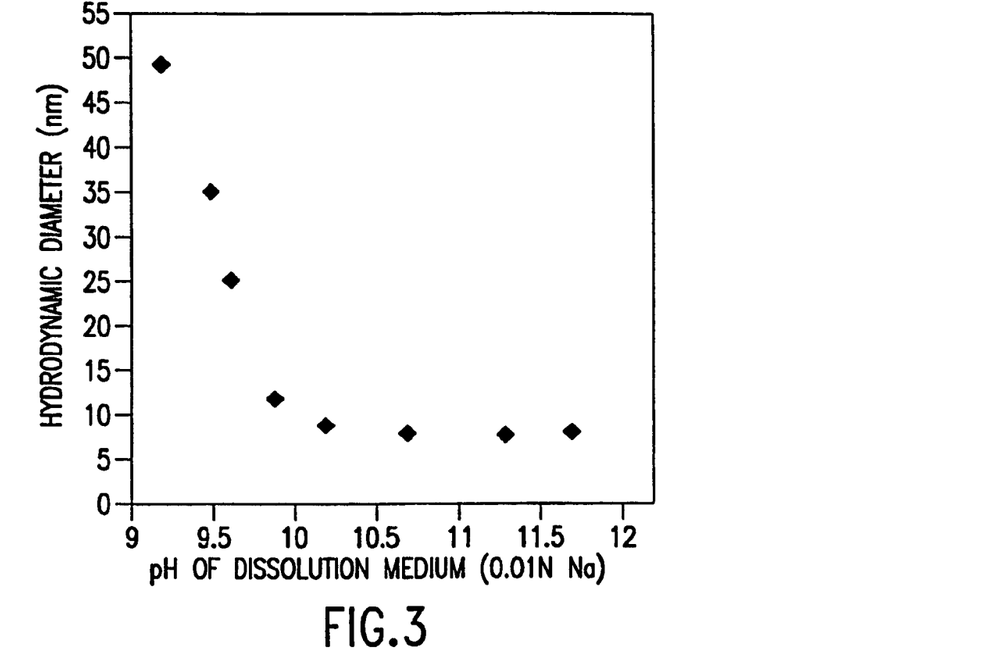
FIG. 3 is a graph showing the micelle hydrodynamic diameter for E5564 in alkaline solutions at constant sodium concentrations via the addition of NaCl.
Figure 4:
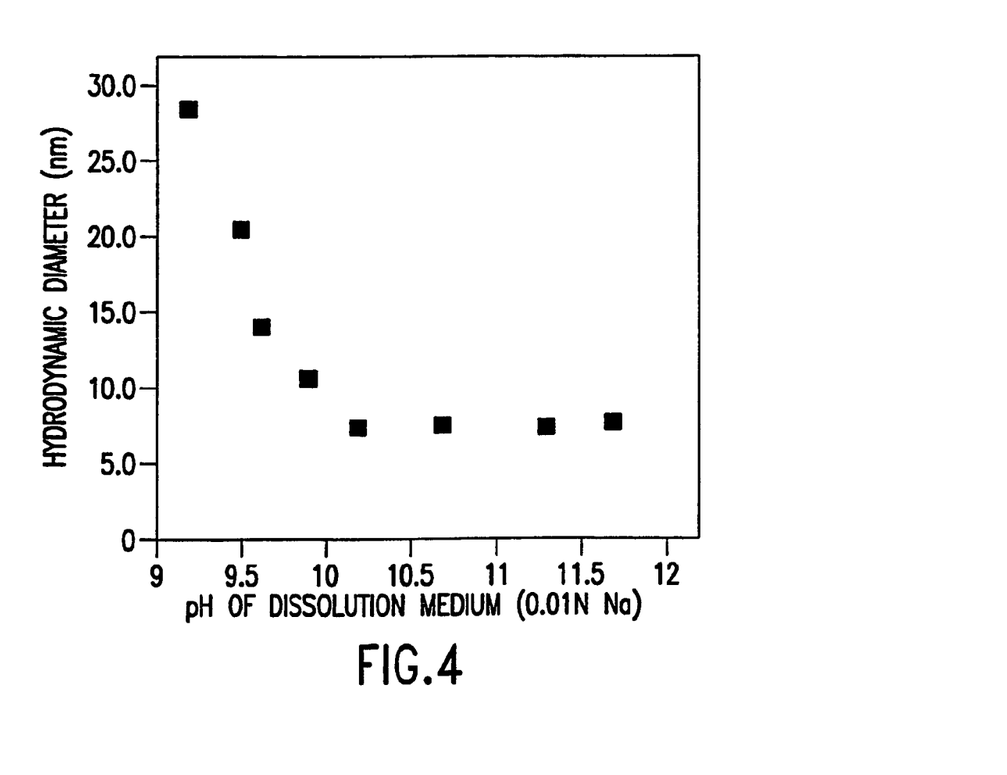
FIG. 4 is a graph showing the relationship between the micelle hydrodynamic diameter for E5564 in a phosphate buffer solution at pH 7.6 after dissolution in NaOH solutions of varying pH and constant sodium concentration (0.01 N Na).

The E5564 micelle hydrodynamic diameter was a monotonically decreasing function of pH in the alkaline solution, as shown in FIG. 3, and unexpectedly produced a micelle having a hydrodynamic diameter as small as 7 nm to 9 nm. Moreover, when the pH of the E5564 alkaline solution was adjusted to pH 7.5 by the addition of a phosphate buffer, the micelle hydrodynamic diameter unexpectedly remained the same (i.e., 7 nm to 9 nm), as shown in FIG. 4. The hydrodynamic diameter of the micelles formed was stable (i.e., fixed) under conditions useful for the manufacture and use of pharmaceutical products. Pharmaceutical preparations are often packaged in vials in a liquid or freeze-dried form. The micelles of fixed hydrodynamic diameters, prepared as described herein, were stable in a liquid or freeze-dried form.

Example 2

Micelles of E5564 having a hydrodynamic diameter of 7 nm to 9 nm (Table 1) prepared as described above were lyophilized. After lyophilization the micelles were reconstituted with water and diluted in an aqueous dextrose solution (Table 2). The micelle hydrodynamic diameter of E5564 in the reconstituted solutions remained at 7 nm to 9 nm in the reconstituted physiologically acceptable solutions under various conditions. The E5564 micelle hydrodynamic diameter was stable when reconstituted in water for 24 hours at 25° C. or 72 hours at 2 to 8° C. The E5564 micelle hydrodynamic diameter was unchanged after admixture with a 5% aqueous dextrose solution maintained at pH 7.4 and storage for 24 hours at 25° C. or 72 hours at 2 to 8° C. (Table 2). The E5564 micelle hydrodynamic diameter was stable as a drug product stored in a lyophilized state at 25° C. under 60% relative humidity, or under refrigeration (Table 3). Further, the E5564 micelle hydrodynamic diameter, in micelles prepared according to the methods of the present invention, was stable under simulated administration conditions using representative infusion equipment (Table 4).

TABLE 1

Micelle Hydrodynamic Diameter Data for
E5564 Solutions Prior to Lyophilization

| sample | hydrodynamic diameter (nm) |
|---|---|
| 1 | 7.6 nm |
| 2 | 7.4 nm |
| 3 | 7.9 nm |

TABLE 2

Micelle Hydrodynamic Diameter of E5564 after Storage
of the Reconstituted and Admixed Solutions

| sample | hydrodynamic diameter (nm) |
|---|---|
| immediately following reconstitution (0.5 mg/mL) | |
| sample-1 | 8.6 |
| sample-2 | 7.7 |
| sample-3 | 6.9 |
| storage for 24 hours at 25° C. | |
| sample-1 | 8.2 |
| storage for 72 hours at 2-8° C. | |
| sample-1 | 8.3 |
| immediately following admixture with 5% dextrose solution (0.14 mg/mL) | |
| sample-1 | 7.7 |
| sample-2 | 6.8 |
| storage for 24 hours at 25° C. | |
| sample-1 | 8.1 |
| storage for 72 hours at 2-8° C. | |
| sample-1 | 7.7 |

TABLE 3

Micelle Hydrodynamic Diameter of E5564 in the Reconstituted
Solution after Storage of the Lyophilized Drug Product

| sample | hydrodynamic diameter (nm) |
|---|---|
| initial | |
| sample-1 | 8.6 |
| sample-2 | 7.7 |
| sample-3 | 6.9 |
| 6 months at 2-8° C. | |
| sample-1 | 7.5 |
| 6 months at 25° C./60% RH | |
| sample-1 | 7.3 |
| sample-2 | 7.2 |

TABLE 4

E5564 Micelle Hydrodynamic Diameter before and after a
Simulated I.V. Infusion using Administration Equipment

| Administration Conditions | Mean Micelle Hydrodynamic Diameter (nm) by DLS |
|---|---|
| 0.5 mg/mL - control | 7.5 |
| 0.5 mg/mL - 1.4 mL/hr - 30 minutes | 7.5 |
| 0.14 mg/mL - control | 7.7 |
| 0.14 mg/mL - 5.0 mL/hr - 30 minutes | 8.7 |

The following conditions apply to the data in Table 4:
Microbore 60" extension set with PVC free fluid path, No.
V6212 (McGraw, Inc.); 3 cc syringe with Luer Lok, No.
309585 (Becton Dickenson); Injection site with Luer Lok,
No. 2N1199 (Baxter); Needle, 20G 1, No. 305175 (Becton
Dickenson); I.V. catheter, JELCO, No. 4050 (Johnson &
Johnson Medical Inc.). "DLS" refers to Dynamic Light Scattering.

Example 3

Figure 2:
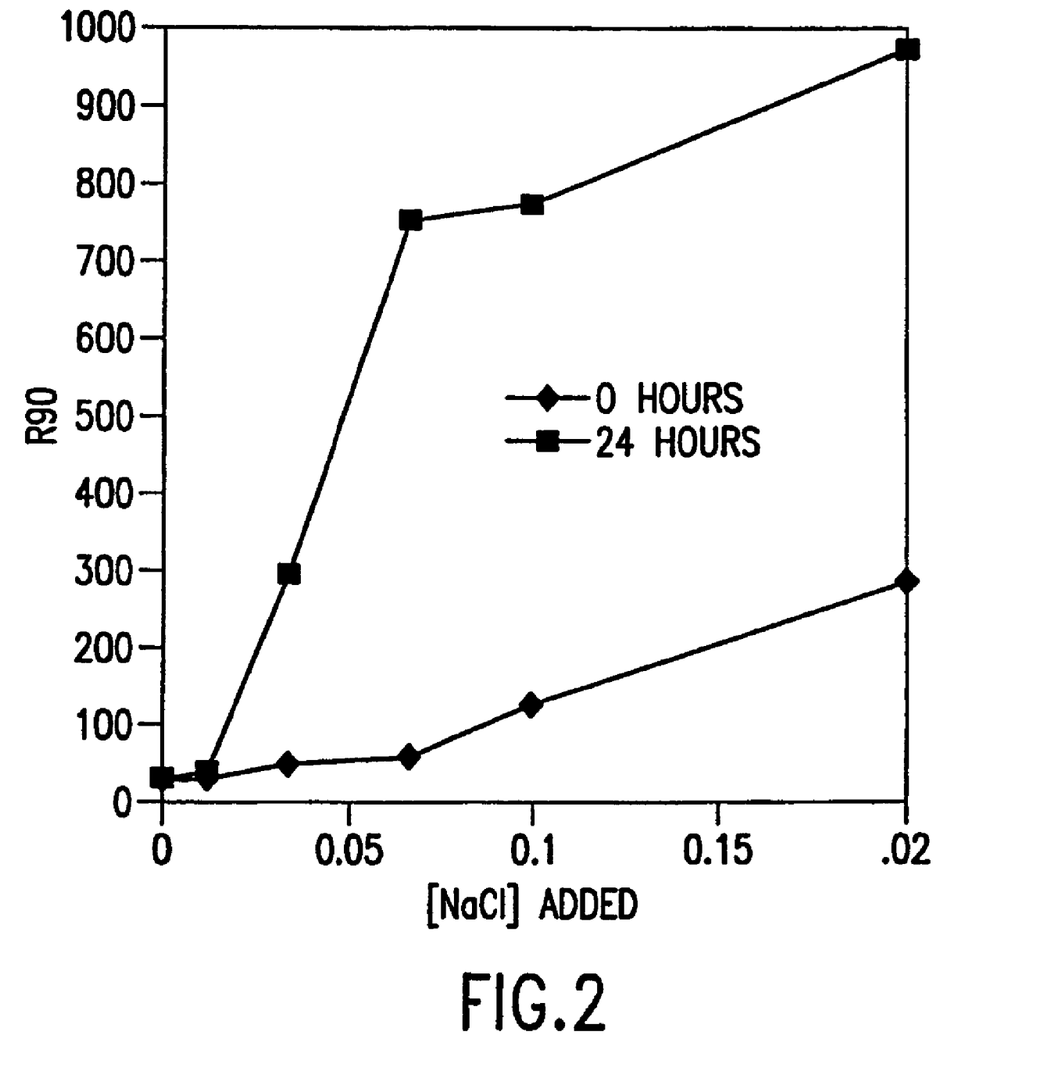
FIG. 2 is a graph showing the increase in micelle hydrodynamic diameter (as measured by an increase in light scattering intensity, R90) with added NaCl.

The micelle hydrodynamic diameter formed utilizing the methods of the invention was destabilized by added salt. FIG. 2 shows the increase in micelle hydrodynamic diameter (as measured by an increase in light scattering intensity, R90) with added NaCl. The E5564 micelle hydrodynamic diameter remained unchanged for 24 hours after addition of 0.01 M NaCl. Changes in micelle hydrodynamic diameter were observed after 24 hours with the addition of 0.03 M NaCl or greater. However, up to 0.07 M NaCl was added with no immediately appreciable change in micelle hydrodynamic diameter. Therefore, higher salt concentrations can be added if the required stability time is less than 24 hours.

Example 4

E5564 was dissolved in an aqueous sodium hydroxide solution to a pH of 10.1 to form an E5564 micelle with a hydrodynamic diameter of 7 nm. This solution was then combined with a lactose containing phosphate buffer solution to yield a solution pH of 7-8. The E5564 micelle hydrodynamic diameter in this phosphate buffer solution was 7 nm. This solution was then filtered through a 0.2 μm filter to render the solution sterile in the manner conventional to pharmaceutical manufacturing. The sterile solution was then filled into vials and freeze-dried. The micelle hydrodynamic diameter was stable upon freeze-drying. The freeze-dried product was re-hydrated with water and the E5564 micelle hydrodynamic diameter was 7 nm.

All patents, patent applications, and publications referred to herein are hereby incorporated by reference in their entirety.

Although the present invention has been set forth in detail, one skilled in the art will appreciate that changes and modifications may be made without departing from the spirit and scope of the invention or appended claims.

What is claimed is:

1. A micelle comprising a compound of formula (A), wherein the micelle has a stable hydrodynamic diameter of about 8 nm to about 10 nm; wherein the compound of formula (A) is:

or a pharmaceutically acceptable salt or stereoisomer thereof;
wherein $R^1$ is selected from the group consisting of:

-continued

J-G-K;

J, K and Q are each independently a straight or branched $C_{1-15}$ alkyl; L is O, N or C; M is O or N; G is N, O, S, SO or $SO_2$; $R^2$ is a straight or branched $C_{5-15}$ alkyl; $R^3$ is selected from the group consisting of:

E is N, O, S, SO or $SO_2$; A, B and D are each independently a straight or branched $C_{4-20}$ alkyl group; $R^4$ is a straight or branched $C_{1-15}$ alkyl group or U and V are each independently a straight or branched $C_{2-15}$ alkyl group; W is a hydrogen or a straight or branched $C_{1-5}$ alkyl group; $R^5$ is hydrogen, -J', -J'-OH, -J'-O—K', -J'-O—K'—OH or J'-O—PO(OH)$_2$; J' and K' are each independently a straight or branched $C_{1-5}$ alkyl group; $R^6$ is hydroxy, halogen, a $C_{1-5}$ alkoxy group or a $C_{1-5}$ acyloxy group; $A^1$ and $A^2$ are each independently selected from the group consisting of:

Z is a straight or branched $C_{1-10}$ alkyl group.

2. A micelle comprising a compound of formula (A), wherein the micelle has a stable hydrodynamic diameter of about 9 nm to about 11 nm; wherein the compound of formula (A) is:

or a pharmaceutically acceptable salt or stereoisomer thereof;

wherein $R^1$ is selected from the group consisting of:

J-G-K;

J, K and Q are each independently a straight or branched $C_{1-15}$ alkyl; L is O, N or C; M is O or N; G is N, O, S, SO or $SO_2$; $R^2$ is a straight or branched $C_{5-15}$ alkyl; $R^3$ is selected from the group consisting of:

E is N, O, S, SO or $SO_2$; A, B and D are each independently a straight or branched $C_{4-20}$ alkyl group; $R^4$ is a straight or branched $C_{1-15}$ alkyl group or U and V are each independently a straight or branched $C_{2-15}$ alkyl group; W is a hydrogen or a straight or branched $C_{1-5}$ alkyl group; $R^5$ is hydrogen, -J', -J'-OH, -J'-O—K', -J'-O—K'—OH or J'-O—PO(OH)$_2$; J' and K' are each independently a straight or branched $C_{1-5}$ alkyl group; $R^6$ is hydroxy, halogen, a $C_{1-5}$ alkoxy group or a $C_{1-5}$ acyloxy group; $A^1$ and $A^2$ are each independently selected from the group consisting of:

Z is a straight or branched $C_{1-10}$ alkyl group.

3. The micelle of claim 1 or claim 2, wherein the compound of formula (A) is a compound of formula (B):

or a pharmaceutically acceptable salt or stereoisomer thereof,
wherein $R_A$ is —$CH_2OCH_3$; $R^1$ is —$COCH_2CO(CH_2)_{10}CH_3$; $R^3$ is —$CO(CH_2)_9CH=CH(CH_2)_5CH_3$; and $R^4$ is —$(CH_2)_2CH(OCH_3)(CH_2)_6CH_3$;
wherein $R_A$ is —$CH_2OCH_3$; $R^1$ is —$COCH_2CO(CH_2)_{10}CH_3$; $R^3$ is —$CO(CH_2)_9CH=CH(CH_2)_5CH_3$; and $R^4$ is —$(CH_2)_2CH(OH)(CH_2)_6CH_3$;
wherein $R_A$ is —$CH_2OCH_3$; $R^1$ is —$COCH_2CO(CH_2)_{10}CH_3$; $R^3$ is —$CO(CH_2)_{16}CH_3$; and $R^4$ is —$(CH_2)_2CH(OH)(CH_2)_6CH_3$;
wherein $R_A$ is —$CH_2OCH_3$; $R^1$ is —$COCH_2CHOH(CH_2)_{10}CH_3$; $R^3$ is —$CO(CH_2)_9CH=CH(CH_2)_5CH_3$; and $R^4$ is —$(CH_2)_2CH(OH)(CH_2)_6CH_3$;
wherein $R_A$ is —$CH_2OCH_3$; $R^1$ is —$COCH_2CO(CH_2)_{10}CH_3$; $R^3$ is —$CO(CH_2)_9CH=CH(CH_2)_5CH_3$; and $R^4$ is —$(CH_2)_9CH_3$;
wherein $R_A$ is —$CH_2OCH_3$; $R^1$ is —$CO(CH_2)_9CH=CH(CH_2)_5CH_3$; $R^3$ is —$CO(CH_2)_9CH=CH(CH_2)_5CH_3$; and $R^4$ is —$(CH_2)_2CH(OH)(CH_2)_6CH_3$;
wherein $R_A$ is —$CH_2OCH_3$; $R^1$ is —$CO(CH_2)_{12}CH_3$; $R^3$ is —$CO(CH_2)_9CH=CH(CH_2)_5CH_3$; and $R^4$ is —$(CH_2)_2CH(OH)(CH_2)_6CH_3$;
wherein $R_A$ is —$CH_2OCH_3$; $R^1$ is —$COCH_2CH(OCH_3)(CH_2)_{10}CH_3$; $R^3$ is —$CO(CH_2)_9CH=CH(CH_2)_5CH_3$; and $R^4$ is —$(CH_2)_2CH(OCH_3)(CH_2)_6CH_3$;
wherein $R_A$ is —$CH_2OCH_3$; $R^1$ is —$COCH_2CH(OCH_3)(CH_2)_{10}CH_3$; $R^3$ is —$CO(CH_2)_9CH=CH(CH_2)_5CH_3$; and $R^4$ is —$(CH_2)_2CH(OH)(CH_2)_6CH_3$;
wherein $R_A$ is —$CH_2OCH_3$; $R^1$ is —$COCH_2CH(OH)(CH_2)_{10}CH_3$; $R^3$ is —$CO(CH_2)_9CH=CH(CH_2)_5CH_3$; and $R^4$ is —$(CH_2)_2CH(OCH_3)(CH_2)_6CH_3$; or
wherein $R_A$ is —$CH_3$; $R^1$ is —$COCH_2CO(CH_2)_{10}CH_3$; $R^3$ is —$CO(CH_2)_9CH=CH(CH_2)_5CH_3$; and $R^4$ is —$(CH_2)_2CH(OCH_3)(CH_2)_6CH_3$.

4. A micelle comprising a compound of formula (I), wherein the micelle has a stable hydrodynamic diameter of about 8 nm to about 10 nm; wherein the compound of formula (I) is:

or a pharmaceutically acceptable salt or stereoisomer thereof.

5. A micelle comprising a compound of formula (I), wherein the micelle has a stable hydrodynamic diameter of about 9 nm to about 11 nm; wherein the compound of formula (I) is:

or a pharmaceutically acceptable salt or stereoisomer thereof.

6. The micelle of claim 4 or claim 5, wherein the compound of formula (1) is a compound of formula (IA):

or a pharmaceutically acceptable salt thereof.

7. The micelle of claim 6, wherein both hydrogen atoms in both —OPO(OH)$_2$ groups in the compound of formula (IA) are replaced with sodium.

8. The micelle of claim 4 or claim 5, wherein the stable hydrodynamic diameter is preselected.

9. The micelle of claim 4 or claim 5, wherein the stable hydrodynamic diameter does not change by more than about 1 nm.

10. The micelle of claim 4 or claim 5, wherein the stable hydrodynamic diameter does not change by more than about 0.5 nm.

11. The micelle of claim 4 or claim 5, wherein the stable hydrodynamic diameter does not substantially change after re-hydration or reconstitution.

12. An aqueous solution comprising at least one micelle of claim 4 or claim 5.

13. A pharmaceutical formulation comprising at least one micelle of claim 4 or claim 5.

14. The pharmaceutical formulation of claim 13, wherein more than 50% of the micelles have a stable hydrodynamic diameter of about 8 nm to about 10 nm.

15. A method of delivering at least one micelle to a patient comprising intravenously administering the pharmaceutical formulation of claim 13 to the patient.

16. A method for treating sepsis in a patient in need thereof comprising administering a therapeutically effective amount of the pharmaceutical formulation of claim 13 to the patient.

17. A method for treating endotoxemia in a patient in need thereof comprising administering a therapeutically effective amount of the pharmaceutical formulation of claim 13 to the patient.

18. A method for treating septic shock in a patient in need thereof comprising administering a therapeutically effective amount of the pharmaceutical formulation of claim 13 to the patient.

19. A method for treating at least one symptom of endotoxemia associated with gram negative bacteria in a patient in need thereof comprising administering a therapeutically effective amount of the pharmaceutical formulation of claim 13 to the patient.

20. The method of claim 19, wherein the at least one symptom is selected from the group consisting of fever, inflammation, disseminated intravascular coagulation, hypotension, renal dysfunction, acute renal failure, acute respiratory distress syndrome, adult respiratory distress syndrome, hepatocellular destruction and cardiac failure.

21. A method for treating systemic inflammatory response syndrome in a patient in need thereof comprising administering a therapeutically effective amount of at least one micelle of claim 13 to the patient.

22. A lyophilized drug product comprising a therapeutically effective amount of at least one micelle comprising a compound of formula (I), wherein the micelle, upon reconstitution in an aqueous solution, has a stable hydrodynamic diameter of about 8 nm to about 10 nm, wherein the compound of formula (I) is:

or a pharmaceutically acceptable salt or stereoisomer thereof.

23. A lyophilized drug product comprising a therapeutically effective amount of at least one micelle comprising a compound of formula (I), wherein the micelle, upon reconstitution in an aqueous solution, has a stable hydrodynamic diameter of about 9 nm to about 11 nm, wherein the compound of formula (I) is:

or a pharmaceutically acceptable salt or stereoisomer thereof.

24. The lyophilized drug product of claim 22 or claim 23, wherein the compound of formula (I) is a compound of formula (IA):

(IA)

or a pharmaceutically acceptable salt thereof.

25. The lyophilized drug product of claim 24, wherein both hydrogen atoms in both —OPO(OH)$_2$ groups in the compound of formula (IA) are replaced with sodium.

26. A method for preparing at least one micelle comprising a compound of formula (A) wherein the micelle has a stable hydrodynamic diameter of about 6 nm to about 20 nm; wherein the method comprises:
providing an aqueous solution with a predetermined metal ion concentration, wherein the metal ion concentration is predetermined based upon a matrix of pH values and salt concentrations; and
adding a compound of formula (A) to the aqueous solution, thereby forming at least one micelle;
wherein the compound of formula (A) is:

(A)

or a pharmaceutically acceptable salt or stereoisomer thereof;

wherein R$^1$ is selected from the group consisting of:

J, K and Q are each independently a straight or branched C$_{1-15}$ alkyl; L is O, N or C; M is O or N; G is N, O, S, SO or SO$_2$; R$^2$ is a straight or branched C$_{5-15}$ alkyl; R$^3$ is selected from the group consisting of:

-continued

E is N, O, S, SO or SO$_2$; A, B and D are each independently a straight or branched C$_{4-20}$ alkyl group; R$^4$ is a straight or branched C$_{1-15}$ alkyl group or U and V are each independently a straight or branched C$_{2-15}$ alkyl group; W is a hydrogen or a straight or branched C$_{1-5}$ alkyl group; R$^5$ is hydrogen, -J', -J'-OH, -J'-O—K', -J'-O—K'—OH or J'-O—PO(OH)$_2$; J' and K' are each independently a straight or branched C$_{1-5}$ alkyl group; R$^6$ is hydroxy, halogen, a C$_{1-5}$ alkoxy group or a C$_{1-5}$ acyloxy group; A$^1$ and A$^2$ are each independently selected from the group consisting of:

Z is a straight or branched C$_{1-10}$ alkyl group.

27. A method for preparing a formulation comprising micelles having a stable hydrodynamic diameter of about 6 nm to about 20 nm; wherein the method comprises:
   providing an aqueous solution with a predetermined metal ion concentration, wherein the metal ion concentration is predetermined based upon a matrix of pH values and salt concentrations; and
   adding a compound of formula (A) to the aqueous solution, thereby forming at least one micelle;
wherein the compound of formula (A) is:

or a pharmaceutically acceptable salt or stereoisomer thereof;

wherein R$^1$ is selected from the group consisting of:

J, K and Q are each independently a straight or branched C$_{1-15}$ alkyl; L is O, N or C; M is O or N; G is N, O, S, SO or SO$_2$; R$^2$ is a straight or branched C$_{5-15}$ alkyl; R$^3$ is selected from the group consisting of:

E is N, O, S, SO or SO$_2$; A, B and D are each independently a straight or branched C$_{4-20}$ alkyl group; R$^4$ is a straight or branched C$_{1-15}$ alkyl group or

U and V are each independently a straight or branched C$_{2-15}$ alkyl group; W is a hydrogen or a straight or branched C$_{1-5}$ alkyl group; R$^5$ is hydrogen, -J', -J'-OH, -J'-O—K', -J'-O—K'—OH or J'-O—PO(OH)$_2$; J' and K' are each independently a straight or branched C$_{1-5}$ alkyl group; R$^6$ is hydroxy, halogen, a C$_{1-5}$ alkoxy group or a C$_{1-5}$ acyloxy group; A$^1$ and A$^2$ are each independently selected from the group consisting of:

Z is a straight or branched C$_{1-10}$ alkyl group.

28. The method of claim 26 or claim 27, wherein at least about 50% of the micelles have a stable hydrodynamic diameter of about 6 nm to about 20 nm.

29. The method of claim 26 or claim 27, wherein the compound of formula (A) is a compound of formula (B):

or a pharmaceutically acceptable salt or stereoisomer thereof,
wherein $R_A$ is —CH$_2$OCH$_3$; $R^1$ is —COCH$_2$CO(CH$_2$)$_{10}$CH$_3$; $R^3$ is —CO(CH$_2$)$_9$CH=CH(CH$_2$)$_5$CH$_3$; and $R^4$ is —(CH$_2$)$_2$CH(OCH$_3$)(CH$_2$)$_6$CH$_3$;
wherein $R_A$ is —CH$_2$OCH$_3$; $R^1$ is —COCH$_2$CO(CH$_2$)$_{10}$CH$_3$; $R^3$ is —CO(CH$_2$)$_9$CH=CH(CH$_2$)$_5$CH$_3$; and $R^4$ is —(CH$_2$)$_2$CH(OH)(CH$_2$)$_6$CH$_3$;
wherein $R_A$ is —CH$_2$OCH$_3$; $R^1$ is —COCH$_2$CO(CH$_2$)$_{10}$CH$_3$; $R^3$ is —CO(CH$_2$)$_{16}$CH$_3$; and $R^4$ is —(CH$_2$)$_2$CH(OH)(CH$_2$)$_6$CH$_3$;
wherein $R_A$ is —CH$_2$OCH$_3$; $R^1$ is —COCH$_2$CHOH(CH$_2$)$_{10}$CH$_3$; $R^3$ is —CO(CH$_2$)$_9$CH=CH(CH$_2$)$_5$CH$_3$; and $R^4$ is —(CH$_2$)$_2$CH(OH)(CH$_2$)$_6$CH$_3$;
wherein $R_A$ is —CH$_2$OCH$_3$; $R^1$ is —COCH$_2$CO(CH$_2$)$_{10}$CH$_3$; $R^3$ is —CO(CH$_2$)$_9$CH=CH(CH$_2$)$_5$CH$_3$; and $R^4$ is —(CH$_2$)$_9$CH$_3$;
wherein $R_A$ is —CH$_2$OCH$_3$; $R^1$ is —CO(CH$_2$)$_9$CH=CH(CH$_2$)$_5$CH$_3$; $R^3$ is —CO(CH$_2$)$_9$CH=CH(CH$_2$)$_5$CH$_3$; and $R^4$ is —(CH$_2$)$_2$CH(OH)(CH$_2$)$_6$CH$_3$;
wherein $R_A$ is —CH$_2$OCH$_3$; $R^1$ is —CO(CH$_2$)$_{12}$CH$_3$; $R^3$ is —CO(CH$_2$)$_9$CH=CH(CH$_2$)$_5$CH$_3$; and $R^4$ is —(CH$_2$)$_2$CH(OH)(CH$_2$)$_6$CH$_3$;
wherein $R_A$ is —CH$_2$OCH$_3$; $R^1$ is —COCH$_2$CH(OCH$_3$)(CH$_2$)$_{10}$CH$_3$; $R^3$ is —CO(CH$_2$)$_9$CH=CH(CH$_2$)$_5$CH$_3$; and $R^4$ is —(CH$_2$)$_2$CH(OCH$_3$)(CH$_2$)$_6$CH$_3$;
wherein $R_A$ is —CH$_2$OCH$_3$; $R^1$ is —COCH$_2$CH(OCH$_3$)(CH$_2$)$_{10}$CH$_3$; $R^3$ is —CO(CH$_2$)$_9$CH=CH(CH$_2$)$_5$CH$_3$; and $R^4$ is —(CH$_2$)$_2$CH(OH)(CH$_2$)$_6$CH$_3$;
wherein $R_A$ is —CH$_2$OCH$_3$; $R^1$ is —COCH$_2$CH(OH)(CH$_2$)$_{10}$CH$_3$; $R^3$ is —CO(CH$_2$)$_9$CH=CH(CH$_2$)$_5$CH$_3$; and $R^4$ is —(CH$_2$)$_2$CH(OCH$_3$)(CH$_2$)$_6$CH$_3$; or
wherein $R_A$ is —CH$_3$; $R^1$ is —COCH$_2$CO(CH$_2$)$_{10}$CH$_3$; $R^3$ is —CO(CH$_2$)$_9$CH=CH(CH$_2$)$_5$CH$_3$; and $R^4$ is —(CH$_2$)$_2$CH(OCH$_3$)(CH$_2$)$_6$CH$_3$.

30. The method of claim 26 or claim 27, wherein the compound of formula (A) is a compound of formula (I):

or a pharmaceutically acceptable salt or stereoisomer thereof.

31. The method of claim 26 or claim 27, wherein the compound of formula (A) is a compound of formula (1A):

or a pharmaceutically acceptable salt thereof.

32. The method of claim 31, wherein both hydrogen atoms in both —OPO(OH)$_2$ groups in the compound of formula (IA) are replaced with sodium.

33. The method of claim 26 or claim 27, wherein the matrix of pH values and salt concentrations is the matrix of FIG. 3.

34. The method of claim 26 or claim 27, wherein the metal ion concentration is a concentration of at least one metal ion selected from the group consisting of $Ca^{2+}$, $Mg^{2+}$, $Ba^{2+}$, $Fe^{2+}$, $Fe^{3+}$, $Al^{3+}$, $Mn^{3+}$, $Mn^{2+}$, $Zn^{2+}$, $Cu^{2+}$, $Cu^{+}$, $Ni^{2+}$, $Sn^{2+}$, $Na^{+}$, $Li^{+}$ and $K^{+}$.

35. The method of claim 26 or claim 27, wherein the metal ion concentration is a concentration of at least one metal ion selected from the group consisting of $Na^{+}$, $K^{+}$, $Li^{+}$, $Ca^{2+}$, $Ba^{2+}$, $Mg^{2+}$ and $Al^{3+}$.

36. The method of claim 26 or claim 27, wherein the metal ion concentration is about 0.1M.

37. The method of claim 26 or claim 27, wherein the pH of the aqueous solution is from about 10 to about 12.

* * * * *